United States Patent [19]

Greene

[11] Patent Number: 4,473,582

[45] Date of Patent: Sep. 25, 1984

[54] INSECTICIDAL STICK APPLICATOR AND METHOD

[75] Inventor: C. Lawrence Greene, Boulder Creek, Calif.

[73] Assignee: Zoecon Corporation, Palo Alto, Calif.

[21] Appl. No.: 403,834

[22] Filed: Jul. 30, 1982

Related U.S. Application Data

[63] Continuation-in-part of Ser. No. 178,067, Aug. 14, 1980, abandoned.

[51] Int. Cl.³ ............... A01N 37/00; A01N 37/08; A01N 25/00; B65D 85/84
[52] U.S. Cl. ............... 424/305; 206/524.1; 424/200; 424/225; 424/282; 424/300; 424/304; 424/309; 424/314; 424/352; 424/358; 424/365; 424/DIG. 5
[58] Field of Search ............ 424/68, 78, 358, 305, 424/200, 225, 282, 300, 304, 309, 314, 352, 365, DIG. 5; 206/524.1

[56] References Cited

U.S. PATENT DOCUMENTS

| | | | |
|---|---|---|---|
| 3,130,124 | 4/1964 | Ferris et al. | 424/DIG. 5 |
| 3,154,470 | 10/1964 | Braun et al. | 424/DIG. 5 |
| 3,162,575 | 12/1964 | Lang | 424/DIG. 5 |
| 3,826,232 | 7/1974 | Duffey et al. | 119/157 |
| 4,137,306 | 1/1979 | Rubino et al. | 424/68 |
| 4,229,432 | 10/1980 | Geria | 424/68 |
| 4,271,181 | 6/1981 | Eastburg | 424/276 |

*Primary Examiner*—Douglas W. Robinson
*Attorney, Agent, or Firm*—William B. Walker; Donald Erickson; Jacqueline Larson

[57] ABSTRACT

An insecticidal package for applying a thin film of water-insoluble insecticide to a household surface including a container and insecticidal stick. The stick comprises from 0.25 to 15 weight percent insecticide, from 10 to 65 weight percent of a fatty alkyl monoether of propylene glycol, from 30 to 75 weight percent of monoethanolamide of fatty acid and optional quantities of liquid lubricity agent compatible therewith, the total liquid content not exceeding 65 weight percent.

20 Claims, 1 Drawing Figure

INSECTICIDAL STICK APPLICATOR AND METHOD

CROSS-REFERENCE TO RELATED APPLICATIONS

This is a continuation-in-part of patent application Ser. No. 178,067 filed Aug. 14, 1980 abandoned.

FIELD OF THE INVENTION

This invention relates to a novel insecticidal stick applicator, a novel insecticidal stick formulation and methods for using them for controlling insects. More particularly, it relates to a solid insecticidal stick incorporating a large volume of liquid water-insoluble insecticide solution. When this stick is applied to a solid surface, it leaves a thin, transparent, uniform film of insecticide. The surfaces to be treated are those to which the insect pest is exposed, especially crawling insects.

BACKGROUND OF THE INVENTION

Insects such as cockroaches and ants are a continual problem in homes and institutions, for example. They are difficult to control since they find harborage in many different areas such as behind or under cabinets or appliances, along base-boards and under sinks and countertops. They will readily move to new areas if the harborage becomes unacceptable. The principal methods presently available for control of such pests are aerosol sprays, baits and tapes, each of which has disadvantages.

Aerosol products generally do not have a long residual activity. Also, the spray from aerosols is broadcast widely, going onto surfaces where protection is not sought or where the active ingredient is not wanted. Furthermore, there are flammability or environmental (ozone layer degradation) concerns about aerosol propellants.

Baits provide protection only in a small area surrounding the bait, and insects can easily avoid them. Also, baits cannot be placed in all areas where the insects might walk or find harborage, such as around the periphery of cabinet doors, on the undersides of countertops, or where counters and built-in appliances junction. They cannot be placed where children or pets could find and ingest them.

Tapes are inconvenient. Unless tapes are placed end-to-end in a continuous strip along all areas, insects can walk around the tape and thus avoid the insecticide. Effective taping requires a large number of tapes and is a slow, time consuming procedure. Furthermore, the tapes are highly visible whereas the film produced by the insecticide stick of the present invention is inconspicuous.

The insecticide stick applicator and method of the present invention is characterized by high effectiveness against crawling insects, such as *Blattella germanica* (German cockroach) and *Periplaneta americana* (American cockroach); long residual activity; ease and convenience of use; suitability for application to any surface; ease of accurate and exact placement; coverage of a large surface area with a uniform, thin, transparent film; and storage stability.

DESCRIPTION OF THE PRIOR ART

U.S. Pat. No. 3,162,575 discloses a fly stick having a microcrystalline wax base mixed with mineral oil, sugar and an insecticide to be applied to the face of domestic livestock. U.S. Pat. No. 3,826,232 also describes a solid pest control stick for application to the neck or face of domestic animals; it comprises a mixture of fatty alcohol, fatty acid, polyalkylene glycol and insecticide. These sticks do not leave a thin, uniform, transparent film of insecticide solution on a solid surface to which they are applied.

Offenlegungsschrift No. 2,038,024 discloses a solid insect combatting carrier having a solid waxlike base containing DDVP (dimethyl dichlorovinyl phosphate) in high concentrations for slow release by insecticide vaporization. Included in the various compositions are mixtures of insecticide and stearic acid monoethanolamide. The insect containing mass is placed in an area to be treated with insecticide, and the insecticide provides prolonged insecticidal activity in the form of vapor. The compositions disclosed therein do not have the physical properties needed for use in a stick applicator and do not leave a uniform thin film when rubbed on a solid support surface, being instead designed as a rigid article for release of insecticide vapor where diffusion of insecticide is critical.

U.S. Pat. No. 4,137,306 describes an antiperspirant stick composition for applying an aluminum salt astringent. Stearic acid monoethanolamide is described as a component of the stick. It does not relate to solid insecticidal sticks or solutions of insecticide.

The prior art compositions are not effective to apply a uniform thin transparent film of water-insoluble insecticide dissolved in a fatty alkyl monoether of propylene glycol to a solid surface.

SUMMARY OF THE INVENTION

One embodiment of this invention is an insecticidal package comprising a container enclosing a solid insecticidal stick. The container is impervious to the components of the insecticidal stick and incudes a means for exposing a portion of the insecticidal stick for application to a solid surface. The solid insecticidal stick comprises from 0.25 to 15 weight percent insecticide, from 10 to 65 weight percent of a fatty hydrocarbon monoether of propylene glycol, and as solid matrix former, from 30–75 weight percent of a monoethanolamide of fatty acid. The stick has physical stability as measured by the 50° C. Storage Stability Test, Heat-Cool Stability Test and Freeze-Thaw Stability Test and leaves a uniform, transparent film on both light and dark, smooth surfaces.

The insecticidal package preferably has parallel side walls, an opening, and a cap means cooperating with the container wall to provide a sealed closure. It also preferably contains means for propelling an adjusted amount of insecticidal stick through the opening for application to a solid surface. For use with such containers, the insecticidal stick can include from 0 to 55 weight percent of a liquid lubricity agent compatible with the other stick components, the combined amount of the fluid components in the stick not exceeding 65 weight percent. In this composition, the preferred insecticides are the pyrethroids, carbamates and insect growth regulators. Holding the insecticidal applicator, the insecticidal stick is rubbed against a solid surface to form a thin, uniform, transparent film of liquid solvent containing insecticide.

DETAILED DESCRIPTION OF THE INVENTION

Figure 1:
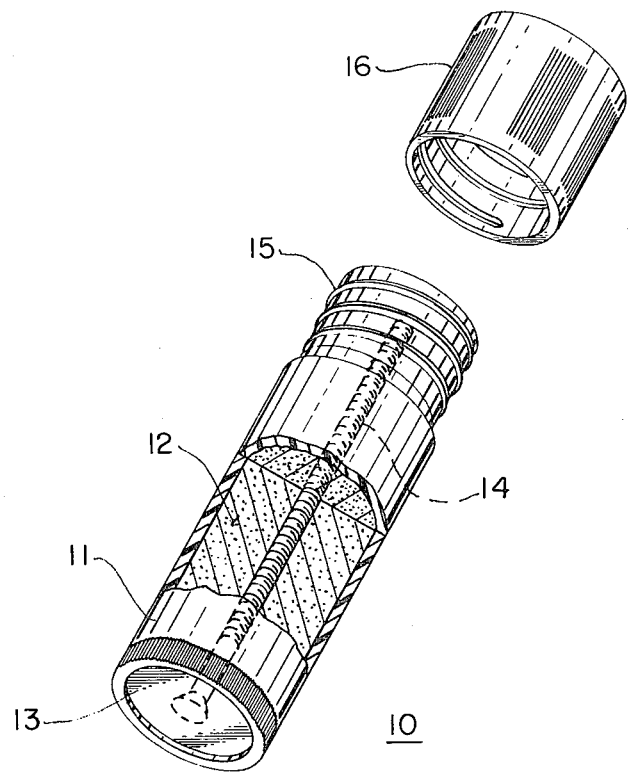
FIG. 1 is a perspective view of an insecticidal package made in accordance with the present invention.

Referring to FIG. 1, the pest control package 10 comprises a cylindrical, tube-like receptacle 11 made from plastic, coated paper, metal or equivalent material which is impervious to the insecticidal stick composition of this invention. The insecticidal stick composition 12 made in accordance with the present invention is liquid when heated and can be poured into the tube-like receptacle and allowed to cool to a solid form in position therein. It substantially fills the interior of the receptacle 11 in a loose press-fit relationship. Upon cooling, the composition shrinks slightly, permitting the solid insecticidal stick composition of this invention to slide easily in the tube-like receptacle. The receptacle 11 shown has a cylindrical shape, but it can have other cross-sectional shapes such as oval or square configurations. Preferably the side walls are parallel so that the insecticidal stick is supported in all positions of extension from the receptacle 11. One end of the receptacle 11 is provided with a cylindrical operating disk 13, the central area of such disk receiving one end of a threaded stem 14 which extends centrally into the solid insecticidal stick composition. Stem 14 is provided with a stop means which will prevent any axial movement with respect to the receptacle 11 and serves, upon rotation of the disk 13 in a first direction, to push the free end of the solid stick 12 beyond the upper free end of the receptacle 11 to provide an exposed portion of the insecticidal stick composition for application to a solid support surface. The insecticidal stick composition 12 can be retracted into the receptacle by rotating the disc 13 in a reverse direction. The opening at the free end of the receptacle 11 is provided with external threads 15 adapted to engage matching elements of a cap 16 in sealing engagement. U.S. Pat. No. 2,818,167 describes a suitable receptacle package, and the entire contents thereof are hereby incorporated by reference.

The insecticidal stick composition of this invention comprises three essential components—the insecticide, fatty hydrocarbon monoether of propylene glycol, and monoethanolamide of fatty acid. A fourth optional component is lubricity agent.

The insecticidally active ingredient in the compositions of the present invention is generally water-insoluble and is physically and chemically stable in the formulation of this invention. It can include, but is not limited to, the synthetic pyrethroids such as permethrin, (3-phenoxy-phenyl)methyl 3-(2,2-dichloroethenyl)-2,2-dimethyl-cyclopropanecarboxylate; fenvalerate, α-cyano-3-phenoxybenzyl 2-(4-chlorophenyl)-3-methylbutanoate; α-cyano-3-phenoxybenzyl 2-(4-difluoromethoxyphenyl)-3-methylbutanoate; α-cyano-3-phenoxybenzyl 2-(2-fluoro-4-trifluoromethylphenylamino)-3-methylbutanoate; and fluvalinate, α-cyano-3-phenoxybenzyl 2-(2-chloro-4-trifluoromethylphenylamino)-3-methylbutanoate. Also included are the carbamates such as propoxur, 2-isopropoxyphenyl methylcarbamate; carbaryl, 1-naphthyl N-methylcarbamate; bendiocarb, 2,2-dimethyl-1,3-benzodioxol-4-yl methylcarbamate; and methomyl N-[[(methylamino)carbonyl]oxy]ethanimidothioate. Suitable insect growth regulators include methoprene, isopropyl (E,E)-11-methoxy-3,7,11-trimethyl-2,4-dode-cadienoate; hydroprene, ethyl (E,E)-3,7,11-trimethyl-2,4-dodecadienoate; and kinoprene, 2-propynyl (E,E)-3,7,11-trimethyl-2,4-dodecadienoate. Suitable phosphates include fenitrothion, O,O-dimethyl O-(4-nitro-m-tolyl) phosphorothioate; phosmet, O,O-dimethyl S-phthalimidomethyl phosphorodithioate; and chlorpyrifos, O,O-diethyl O-(3,5,6-trichloro-2-pyridyl) phosphorothioate. Chlorinated pesticides which can be used include lindane, 1,2,3,4,5,6-hexachlorocyclohexane. The concentration of the active ingredient present in the formulation can range from 0.25 to 15 weight percent and is preferably from 2 to 5 weight percent. A single active ingredient or a mixture of active ingredients can be included in the formulation.

The composition also contains from 10 to 65 and preferably from 15 to 33 weight percent of fatty hydrocarbon monoether of propylene glycol. This can include fatty alkyl and alkenyl monoethers having from 14 to 22 carbon atoms, and are derived from fatty acids, saturated or unsaturated. Propylene glycol-3-myristyl ether is a preferred compound.

The propylene glycol ether has been found to be an unexpectedly superior insecticidal solvent vehicle for application to solid support surfaces, in particularly smooth cabinet surfaces, leaving a uniform, thin, virtually invisible transparent film on both dark and light surfaces. Since the insecticides in their natural state are solid or oily liquids at room temperature, their distribution in a thin, uniform, transparent, non-tacky film is a major feature of this invention.

As the third essential component, the insecticidal stick of this invention comprises from 30 to 75 and preferably from 30 to 40 weight percent of monoethanolamide of fatty acid. This compound forms a solid matrix with the solution of insecticide in the propylene glycol ether described above. The monothanolamides of fatty acids include saturated or unsaturated compounds having from 15 to 22 carbon atoms in the fatty acid group. One or more of the monoethanolamides in this group can be used. Preferred monoethanolamides include coco monoethanolamide and stearic monoethanolamide, for example.

The monoethanolamide is particularly compatible with the other two components to yield a physically stable, solid stick composition of insecticide solution in a matrix. It is critical that the composition be free from sweating, cracking, drying, or loss of homogeneity and the film formation not be accompanied by flaking, cracking, uneven film deposition or deposit of a visible residue.

Optional components in the insecticidal stick composition of the invention are lubricity agents. These facilitate movement of the insecticidal stick within the package receptacle and facilitate uniform application to solid support surfaces. From 0 to 55 weight percent and preferably from 18 to 42 weight percent of the lubricity agent can be used, the total liquid content of the insecticidal stick not exceeding 65 weight percent and preferably being from 55 to 65 weight percent. A variety of liquids can be used as the lubricity agent. The preferred liquids are non-polar and include silicone oils (polysiloxanes), mineral oils and mixtures thereof.

The composition is substantially made from non-polar liquids. Minor amounts of water (up to 10 weight percent) can be tolerated in some compositions, particularly those containing polysiloxanes.

Depending on the active insecticide use, a pH adjuster may be required to make the formulation netural or slightly acid. For example, when permethrin is included as the active ingredient, the formulation should have a pH of 4 to 7 and stearic acid can be added to provide a slightly acid pH.

An alternate form of this invention comprises having the insecticidal stick composition in the form of a crayon. The crayon can be molded from the formulation to have a cylindrical or polygonal form of 3 or more sides. A strippable, protective wrapping such as paper or plastic can be used to enclose the crayon. However, for application of the insecticidal stick of this invention in a form designed for repeated use (and storage between uses) or for use in a household environment, an applicator such as described in FIG. 1 is preferred. It protects the insecticidal stick in a sealed container during storage and reduces the risk of skin contact or accidental ingestion by children.

For using the applicator of the present invention, the formulation containing the active ingredient in an insecticidally effective amount is rubbed onto the surface to be treated, usually along areas where the target insects have been seen or where they may find harborage. A thin film of the formulation is thereby deposited on the surface (e.g., a baseboard or inner surface) of storage cabinets, thus providing a point of contact for control of the insects. Without any intention of being bound by theory, it is believed that the formulation is effective by reason of the insect walking or crawling over the film and the insecticide being ingested or absorbed through the cuticle of the insect.

The formulation of the present invention can also be used to provide invisible protection against fleas by rubbing the formulation on the coats of pet animals. Particularly advantageous compounds as active ingredients in this embodiment are the insect growth regulators, such as methoprene. In the same manner, animals such as horses and cows may be protected against flies such as face flies.

The insecticidal stick of this invention has physical stability as measured by a number of tests.

STABILITY TESTS

50° C. Storage Stability Test

The insecticidal applicator is maintained at a temperature of 50° C. and the insecticidal stick is examined for physical changes every 2 months for 6 months.

Heat-Cool Stability Test

The insecticidal applicator is subjected to a repeated cycle of alternately heating at 40° C. for 12 hours and then cooling to 25° C. for 12 hours. The insecticidal stick is examined for physical changes every 2 months for 12 months.

Freeze-Thaw Stability Test

The insecticidal applicator is subjected to a temperature cycle of −21° C. for 24 hours and then 25° C. for 24 hours, repeated for 3 cycles, and the insecticidal stick is examined for physical change.

The examination for physical change in the above tests is made by examining the stick and evaluating the properties of the residue deposited when the stick is rubbed on a smooth surface. Any evidence of stick sweating, cracking, drying, or any loss of stick homogeneity constitutes a test failure. During film formation, any flaking, crumbling, excessive and uneven film deposition or deposition of a visible (conspicuous) residue on a smooth light or dark surface constitutes a test failure.

The following examples are provided to illustrate the practice of the present invention. Temperatures are provided in degrees Centigrade and percentages as weight percents unless otherwise specified.

EXAMPLE 1

| Ingredient | Weight % |
|---|---|
| Stearic monoethanolamide[a] | 26.1 |
| Stearic monoethanolamide stearate[b] | 12.2 |
| Propylene glycol-3-myristyl ether[c] | 15.2 |
| Mineral Oil | 36.0 |
| Petrolatum | 6.0 |
| (3-Phenoxyphenyl)methyl(±)cis/trans-3-(2,2-dichloroethenyl)-2,2-dimethylcyclopropanecarboxylate[d] | 2.5 |
| Stearic acid | 2.0 |

[a]Witcamide 70 (Witco Chemical)
[b]Witcamide MAS (Witco Chemical)
[c]Witconol APM (Witco Chemical)
[d]Permethrin - cis/trans isomer ratio = 75/25 ± 5

The propylene glycol ether, mineral oil, petrolatum and (3-phenoxyphenyl)methyl 3-(2,2-dichloroethenyl)-2,2-dimethylcyclopropanecarboxylate are added to a container equipped with a stirrer, a thermometer and a heating device. The mixture is heated, with stirring, to 90–95°. The momoethanolamide, the monoethanolamide stearate and the stearic acid are then slowly added, maintaining the temperature between 85° and 95°. When a homogenous liquid is yielded, the solution is cooled to 86–90°. When this temperature is reached, the liquid is poured into a mold or into an applicator container. This is allowed to cool at room temperature or below until it is solid throughout.

EXAMPLE 2

A. The procedure of Example 1 is followed using the ingredients listed below.

| Ingredient | Weight % |
|---|---|
| Coconut monoethanolamide | 34.0 |
| Propylene glycol-3-myristyl ether | 33.0 |
| Polydimethylcyclosiloxane[a] | 18.0 |
| Water | 8.0 |
| (3-Phenoxyphenyl)methyl 3-(2,2-dichloroethenyl)-2,2-dimethylcyclopropanecarboxylate | 5.0 |
| Stearic acid | 2.0 |

[a]Cyclomethicone; Silicon 344 (Dow Corning)

B. In the same way, there is prepared the following composition.

| Ingredient | Weight % |
|---|---|
| Coconut monoethanolamide | 56.0 |
| Stearic monoethanolamide | 15.0 |
| Propylene glycol-3-myristyl ether | 25.0 |
| 2-Isopropoxyphenyl methylcarbamate[a] | 2.0 |
| Stearic acid | 2.0 |

[a]Propoxur

EXAMPLE 3

The above formulation is prepared as described, but with the compound α-cyano-3-phenoxybenzyl 2-(4-difluoromethoxy)-3-methylbutanoate as the active ingredient rather than methoprene.

| Ingredient | Weight % |
| --- | --- |
| Stearic monoethanolamide | 35.0 |
| Propylene glycol-3-myristyl ether | 34.0 |
| Polydimethylcyclosiloxane | 19.0 |
| Water | 8.0 |
| 2,2-Dimethyl-1,3-benzodioxol-4-yl methyl-carbamate[a] | 2.0 |
| Stearic acid | 2.0 |

[a]Bendiocarb

EXAMPLE 4

Following the procedure of EXAMPLE 1, the composition below is prepared.

| Ingredient | Weight % |
| --- | --- |
| Stearic monoethanolamide | 28.6 |
| Stearic monoethanolamide stearate | 12.2 |
| Propylene glycol-3-myristyl ether | 15.2 |
| Petrolatum | 6.0 |
| Mineral Oil | 36.0 |
| Isopropyl (E,E-11-methoxy-3,7,11-trimethyl-2,4-dodecadienoate[a] | 2.0 |

[a]Methoprene

EXAMPLE 5

The stick formulation to be tested is rubbed onto a 6" square glass plate, covering a 4-inch diameter circle with the material. One group of adult *Blatella germanica* (ten adults, mixed sex) is confined on the plate for fifteen minutes. At least two plates are fun for each formulation. The cockroaches are removed after the fifteen-minute exposure period and are observed for percent mortality at 24 hours after exposure.

Formulation A and Formulation B (compositions of which are described below) were tested in this assay. Each formulation gave 95% mortality within 24 hours after exposure.

| Formulation A | |
| --- | --- |
| Ingredient | Weight % |
| Stearic monoethanolamide | 35.0 |
| Propylene glycol-3-myristyl ether | 34.0 |
| Polydimethylcyclosiloxane | 19.0 |
| Water | 8.0 |
| (3-Phenoxyphenyl)methyl(±)cis/trans-3-(2,2-dichloroethenyl)-2,2-dimethylcyclopropane-carboxylate[a] | 2.0 |
| Stearic acid | 2.0 |

[a]cis/trans isomer ratio = 75/25 ± 5

| Formulation B | |
| --- | --- |
| Ingredient | Weight % |
| Stearic monoethanolamide | 26.6 |
| Stearic monoethanolamide stearate | 12.2 |
| Propylene glycol-3-myristyl ether | 15.2 |
| Petrolatum | 6.0 |
| Mineral Oil | 36.0 |
| (3-Phenoxyphenyl)methyl(±)-cis/trans-3-(2,2-dichloroethenyl)-2,2-dimethylcyclopropane-carboxylate[a] | 2.0 |
| Stearic acid | 2.0 |

[a]cis/trans isomer ratio = 75/25 ± 5

EXAMPLE 6

The procedure of Example 1 is followed with the following ingredients.

| Ingredient | Weight % |
| --- | --- |
| Coconut monoethanolamide | 13.0 |
| Stearic monoethanolamide | 58.0 |
| Propylene glycol-3-myristyl ether | 24.5 |
| Permethrin | 2.5 |
| Stearic acid | 2.0 |

EXAMPLE 7

The formulations of the preceding examples when tested according to the Stability Tests described hereinabove satisfy the test criterion set forth therein for physical stability and effective film formation.

EXAMPLE 8

The formulations of Examples 1, 3 and 6 are applied to a variety of smooth surfaces, and the film visibility is determined by a visual examination and judged on a scale of 0 to 5, 0 being invisible and 5 being highly visible. The results are as follows:

| Example No. | 1 | 3 | 6 |
| --- | --- | --- | --- |
| Smooth Surface | | | |
| Dark green ceramic tile | 0 | 1 | 0 |
| White ceramic tile | 0 | 0 | 0 |
| Vinyl wallpaper | 0 | 0 | 0 |
| Brown formica | 0 | 0 | 0 |
| White formica | 0 | 0 | 0 |

On rougher surfaces, the results were varied as indicated below:

| Example No. | 1 | 3 | 6 |
| --- | --- | --- | --- |
| Surface | | | |
| Brown enamel on particle board | 0 | 3 | |
| White latex on particle board | 0 | 0 | 0 |
| White enamel on particle board | 0 | 0 | 0 |
| Unfinished particle board | 5 | 3 | 4 |
| Brown enamel on plywood | 1 | 3 | 2 |
| White latex on plywood | 0 | 0 | 0 |
| Green latex on plywood | 0 | 0 | 0 |
| Light brown stain on plywood | 1 | 0 | 1 |
| White enamel on plywood | 0 | 0 | 0 |
| Unfinished plywood | 4 | 2 | 2 |

Invisibility to low visibility was observed on light surfaces and moderately smooth dark surfaces.

The invention claimed is:

1. An insecticidal package comprising a container enclosing a solid insecticidal stick, the container being impervious to the components of the insecticidal stick and including means for exposing a portion of the insecticidal stick, the solid insecticidal stick comprising
   (a) from 0.25 to 15 weight percent of a water-insoluble insecticide,
   (b) from 10 to 65 weight percent of a fatty hydrocarbon monoether of propylene glycol, and
   (c) from 30 to 75 weight percent of a monoethanolamide of a fatty acid,
the stick being physically stable and leavling a uniform, transparent film on smooth surfaces.

2. The insecticidal package of claim 1 wherein the container has parallel side walls and an end opening, a cap means cooperating with the container walls to provide a sealed closure for the opening, and means for propelling the insecticidal stick through the opening for application to a solid surface.

3. The insecticidal package of claim 2 wherein the insecticidal stick includes from 0 to 55 weight percent of a liquid lubricity agent compatible with the other stick components, the combined amount of the liquid components in the insecticidal stick not exceeding 65 weight percent.

4. The insecticidal package of claim 3 wherein the insecticide is a synthetic pyrethroid, a carbamate, insect growth regulator, or a mixture thereof.

5. The insecticidal package of claim 1 wherein the insecticide is a synthetic pyrethroid selected from the group consisting of (3-phenoxyphenyl)methyl 3-(2,2-dichloroethenyl)-2,2-dimethylcyclopropanecarboxylate, α-cyano-3-phenoxy-benzyl 2-(4-chlorophenyl)-3-methylbutanoate, α-cyano-3-phenoxybenzyl 2-(2-fluoro-4-trifluoromethylphenylamino)-3-methylbutanoate, and α-cyano-3-phenoxybenzyl 2-(2-chloro-4-trifluoromethylphenylamino)-3-methylbutanoate and mixtures thereof.

6. The insecticidal package of claim 5 wherein the insecticidal stick composition comprises
   (a) from 2 to 5 weight percent of a synthetic pyrethroid insecticide,
   (b) from 15 to 33 weight percent of a fatty hydrocarbon monoether of propylene glycol,
   (c) from 30 to 40 weight percent of a monoethanolamide of a fatty acid, and
   (d) from 18 to 42 weight percent of a lubricity agent, the amount of combined liquid in the insecticidal stick being within the range of from 55 to 65 weight percent.

7. The insecticidal package of claim 6 wherein the insecticide is (3-phenoxyphenyl)methyl 3-(2,2-dichloroethenyl)-2,2dimethylcyclopropanecarboxylate.

8. A solid insecticidal stick comprising
   (a) from 0.25 to 15 weight percent of a water-insoluble insecticide,
   (b) from 10 to 65 weight percent of a fatty hydrocarbon monoether of propylene glycol, and
   (c) from 30 to 75 weight percent of a monoethanolamide of a fatty acid,
the stick physically stable and leaving a uniform, transparent film on smooth surfaces.

9. The insecticidal stick of claim 8 including from 0 to 55 weight percent of a liquid lubricity agent compatible with the other stick components, the combined amount of the liquid components in the insecticidal stick not exceeding 65 weight percent.

10. The insecticidal stick of claim 9 wherein the insecticide is a synthetic pyrethroid, a carbamate, insect growth regulator, or a mixture thereof.

11. The insecticidal stick of claim 8 wherein the insecticide is a synthetic pyrethroid selected from the group consisting of (3-phenoxyphenyl)methyl 3-(2,2-dichloroethenyl)-2,2-dimethylcyclopropanecarboxylate, α-cyano-3-phenoxy-benzyl 2-(4-chlorophenyl)-3-methylbutanoate, αcyano-3-phenoxybenzyl 2-(2-fluoro-4-trifluoromethylphenylamino)-3-methylbutanoate, and α-cyano-3-phenoxybenzyl 2-(2-chloro-4-trifluoromethylphenylamino)-3-methylbutanoate and mixtures thereof.

12. The insecticidal stick of claim 8 wherein the insecticidal stick composition comprises
   (a) from 2 to 5 weight percent of a synthetic pyrethroid insecticide,
   (b) from 15 to 33 weight percent of a fatty hydrocarbon monoether of propylene glycol,
   (c) from 30 to 40 weight percent of a monoethanolamide of a fatty acid, and
   (d) from 18 to 42 weight percent of a lubricity agent, the amount of combined liquid in the insecticidal stick being within the range of from 55 to 65 weight percent.

13. The insecticidal stick of claim 12 wherein the insecticide is (3-phenoxyphenyl)methyl 3-(2,2-dichloroethenyl)-2,2-dimethylcyclopropanecarboxylate.

14. A method for control of insects wherein a solid insecticidal stick is rubbed on a solid surface to leave a thin, uniform transparent film of solution containing insecticide thereon, the insecticidal stick comprising
   (a) from 0.25 to 15 weight percent of a water-insoluble insecticide,
   (b) from 10 to 65 weight percent of a fatty hydrocarbon monoether of propylene glycol, and
   (c) from 30 to 75 weight percent of a monoethanolamide of a fatty acid.

15. The method of claim 14 wherein the insecticidal stick is enclosed in a container having parallel side walls, an end opening, a cap means cooperating with the container walls to provide a sealed closure for the opening, and means for propelling the insecticidal stick through the opening for application to a solid surface.

16. The method of claim 15 wherein the insecticidal stick includes from 0 to 55 weight percent of a liquid lubricity agent compatible with the other stick components, the combined amount of the liquid components in the insecticidal stick not exceeding 65 weight percent, whereby movement of the insecticidal stick in the container is facilitated.

17. The method of claim 16 wherein the insecticide is a synthetic pyrethroid, a carbamate, insect growth regulator, or mixture thereof.

18. The method of claim 14 wherein the insecticide is a synthetic pyrethroid selected from the group consisting of (3-phenoxyphenyl)methyl 3-(2,2-dichloroethenyl)-2,2-dimethylcyclopropanecarboxylate, α-cyano-3-phenoxy-benzyl 2-(4-chlorophenyl)-3-methylbutanoate, α-cyano-3-phenoxybenzyl 2-(2-fluoro-4-trifluoromethylphenylamino)-3-methylbutanoate, and α-cyano-3-phenoxybenzyl 2-(2-chloro-4-trifluoromethylphenylamino)-3-methylbutanoate and mixtures thereof.

19. The method of claim 18 wherein the insecticidal stick composition comprises
   (a) from 2 to 5 weight percent of a synthetic pyrethroid insecticide,
   (b) from 15 to 30 weight percent of a fatty hydrocarbon monoether of propylene glycol,
   (c) from 30 to 40 percent of a monoethanolamide of a fatty acid, and
   (d) from 18 to 42 weight percent of a lubricity agent, the amount of combined liquid in the insecticidal stick being within the range of from 55 to 65 weight percent.

20. The method of claim 6 wherein the insecticide is (3-phenoxyphenyl)methyl 3-(2,2-dichloro-ethenyl)-2,2-dimethylcyclopropanecarboxylate.

* * * * *